United States Patent
Binder

(10) Patent No.: US 8,063,253 B2
(45) Date of Patent: Nov. 22, 2011

(54) PROCESS FOR THE CRYSTALLISATION OF MESOTRIONE

(75) Inventor: Arthur Binder, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 463 days.

(21) Appl. No.: 12/160,813

(22) PCT Filed: Jan. 15, 2007

(86) PCT No.: PCT/IB2007/000198
§ 371 (c)(1),
(2), (4) Date: Jul. 14, 2008

(87) PCT Pub. No.: WO2007/083242
PCT Pub. Date: Jul. 26, 2007

(65) Prior Publication Data
US 2010/0152492 A1    Jun. 17, 2010

Related U.S. Application Data

(60) Provisional application No. 60/759,707, filed on Jan. 18, 2006.

(51) Int. Cl.
*C07C 317/00*    (2006.01)

(52) U.S. Cl. ......................................................... 568/30
(58) Field of Classification Search ..................... 568/30
See application file for complete search history.

(56) References Cited

U.S. PATENT DOCUMENTS

2008/0194880 A1*  8/2008  Dawson et al. ................. 568/31

FOREIGN PATENT DOCUMENTS

| WO | 2002076934 | 10/2002 |
| WO | 2005035487 | 4/2005 |
| WO | 2005092846 | 10/2005 |
| WO | 2006021743 | 3/2006 |

* cited by examiner

*Primary Examiner* — Porfirio Nazario Gonzalez
(74) *Attorney, Agent, or Firm* — William A. Teoli, Jr.

(57) ABSTRACT

The invention relates to a process for selectively controlling the crystallisation mesotrione [2-(4-methylsulphonyl-2-nitrobenzoyl)cyclohexane-1,3-dione] from aqueous solution in which the aqueous mesotrione solution is introduced to a crystalliser containing seed crystals predominantly of the thermodynamically stable polymorph ("Form 1") in a semi-continuous or continuous manner. The invention further relates to a process for converting the metastable polymorph ("Form 2") of mesotrione to Form 1 by introducing an aqueous solution containing the former form to a crystalliser containing seed crystals predominantly of the latter form.

3 Claims, 2 Drawing Sheets

US 8,063,253 B2

PROCESS FOR THE CRYSTALLISATION OF MESOTRIONE

This application is a 371 of International Application No. PCT/IB2007/000198 filed Jan. 15, 2007, which claims priority to U.S. 60/759,707 filed Jan. 18, 2006, the contents of which are incorporated herein by reference.

FIELD OF THE INVENTION

The invention relates to a process for selectively controlling the crystallization of polymorphic forms of mesotrione. The invention further relates to the use of a semi-continuous or continuous process to control polymorphic formation. The invention further relates to a process for converting one polymorphic form to another.

BACKGROUND

The protection of crops from weeds and other vegetation that inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Commercial herbicides and some that are still in development are described in The Pesticide Manual, 13$^{th}$ Edition, published 2003 by the British Crop Protection Council.

Many herbicides also damage crop plants. The control of weeds in a growing crop therefore requires the use of so-called 'selective' herbicides, which are chosen to kill the weeds while leaving the crop undamaged. In practice, few herbicides are, fully selective, in that they will kill all the weeds and leave the crop untouched at a particular application rate. The use of most selective herbicides is actually a balance between applying enough herbicides to acceptably control most of the weeds and causing only minimal crop damage. One known selective herbicide is mesotrione (2-(4-methyl-sulphonyl-2-nitrobenzoyl)cyclohexane-1,3-dione).

It is well known that certain substances can form different crystal structures, or polymorphs. In many cases, only one of the polymorphs is thermodynamically stable. Mesotrione, a broadleaf herbicide, is an example of a substance that can form polymorph crystals. Crystallization of mesotrione is carried out by a pH shift in a predominantly aqueous solution whereby the soluble salt is converted to the insoluble free acid resulting in high yield. It has recently been discovered that mesotrione exists in two polymorphic forms: the thermodynamically stable form, referred to herein as Form 1; and the metastable form, referred to herein as Form 2.

For aqueous crystallization a large difference in size between Form 1 and Form 2 mesotrione was seen and this is a very useful technique for assessing the presence of Form 2. The powder X Ray Diffraction (PXRD) patterns and data for the two polymorphic forms are also distinctly different In the commercial manufacture of mesotrione it is important to produce the thermodynamically stable polymorph, referred to as Form 1. However, due to the size of the crystals, milling is required to reduce the crystal size when formulating into an agrochemically acceptable composition. Form 2 is already of a size that would be suitable for formulating into an agrochemically acceptable composition, however, Form 2 is thermodynamically unstable and would gradually convert to Form 1; consequently any formulation prepared therefrom can lead to instability problems during storage, or it can result in difficulties during the application of the product in the field.

A further problem exists in that Form 1 is currently the form used in preparing agrochemically acceptable formulations, but during the manufacturing process, Form 2 is readily made when mesotrione is recrystallized in aqueous solution. Due to Form 2 being very fine, it is difficult to harvest the solids and production time is lost while trying to remove it from the system. If the Form 2 material obtained during recrystallization cannot be converted to Form 1, then it must be disposed of, resulting in lost revenue and inefficient production processes.

Commercial manufacture of herbicides is often done in batch reactors. Consequently, the crystallization process, which is typically the last stage of the manufacturing process, is also often conducted in a batch mode. In this mode of operation, a small number of batches yield product that contain the undesirable Form 2 crystals. Formation of Form 2 crystals can be avoided by using solvents during the crystallization. However, the use of solvents will significantly increase the manufacturing costs due to the recovery or disposal of these solvents.

WO 03/099409 teaches the use of solvents to control polymorphism. The use of solvents generates a waste stream which can be difficult to treat because of high solvent loadings, or it requires additional process steps and equipment to recover the solvent from the waste stream.

SUMMARY OF THE INVENTION

An object of the invention is to provide a process for selectively producing the Form 1 polymorph of mesotrione.

A second object of the invention is to provide a process for readily converting Form 2 polymorph into Form 1 polymorph.

Accordingly, the present invention provides a process for selectively controlling the crystallization of the Form 1 polymorph of mesotrione from an aqueous mesotrione solution, comprising using a semi-continuous or continuous crystallization process, wherein the crystallization process is conducted in a crystallizer in a semi-continuous or continuous manner and wherein said Form 1 mesotrione is ultimately obtained.

The invention is based on the discovery that the use of a large amount of Form 1 seed crystals in the crystallization process will lead to the reliable manufacture of mesotrione product that consists of the desired Form 1 crystals. The term "large", as used herein, means that the amount of seed crystals used is greater than 50% by weight, preferably at least 70% by weight, of the amount of mesotrione in solution present in the crystallizer (also referred to herein as the crystallization reactor). Carrying out the crystallization process in a semi-continuous or continuous manner provides improved control and processing compared to carrying out the mesotrione crystallization in a batch mode. In the semi-continuous and continuous crystallization mode, the crystallization mother liquor always contains a high concentration of the Form 1 crystals, whereas this is not the case in the batch crystallization process. According to the process of the present invention, mesotrione product with the desired crystal morphology can reliably be produced without the need for solvents by conducting the crystallization in a semi-continuous or continuous manner.

DETAILED DESCRIPTION OF THE INVENTION

Figure 1:
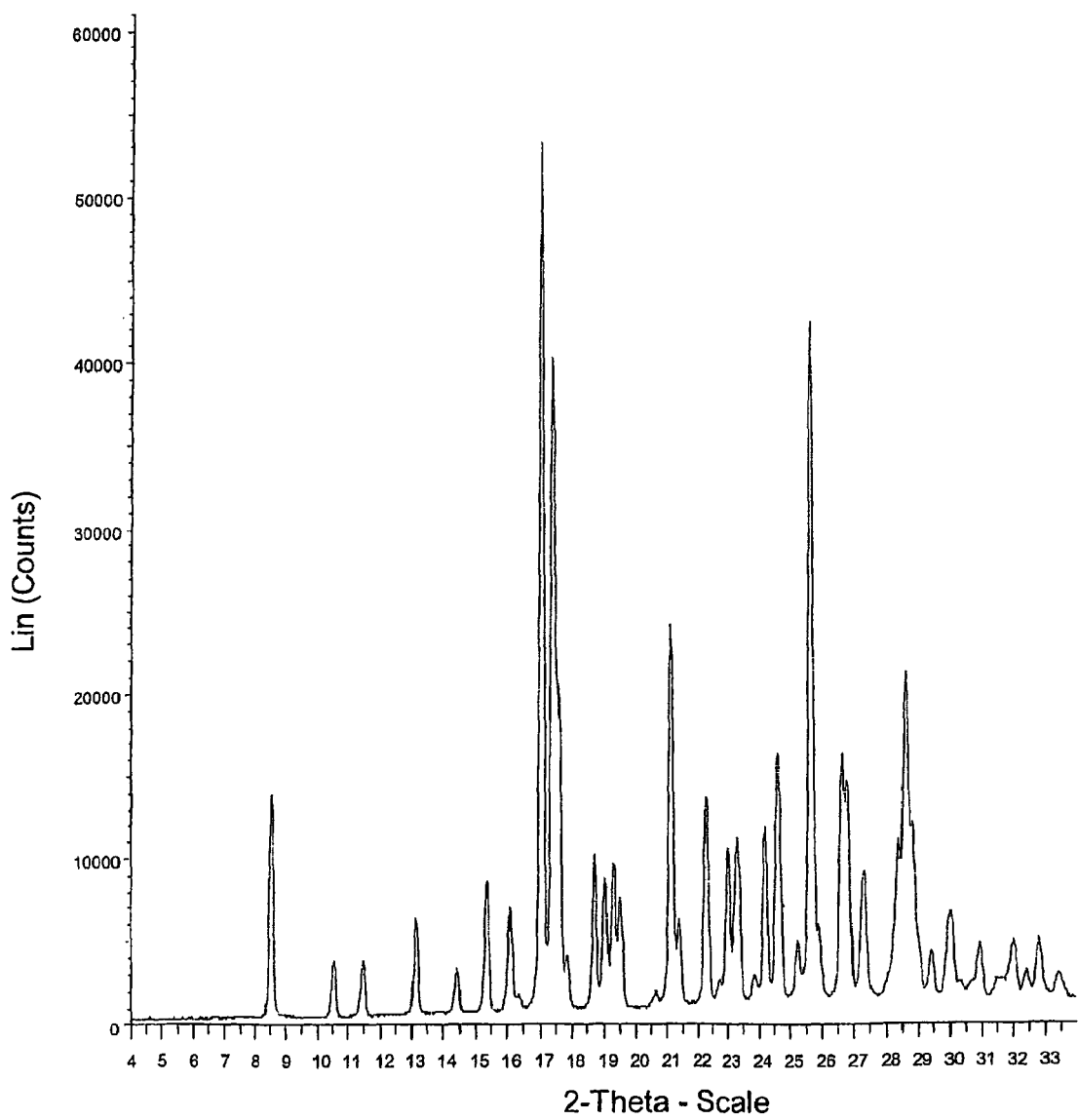
FIG. 1 is a powder X Ray diffraction (PXRD) pattern of Form 1 mesotrione.

Crystallization, of mesotrione is achieved by changing the pH of an alkaline solution, which contains mesotrione in dissolved form, to acidic conditions. Mesotrione is highly soluble at an alkaline pH. As the pH is lowered, the solubility of mesotrione decreases and crystals are formed.

Suitably, the pH of the mesotrione composition is first increased to a pH of >7, suitably $\geq 9$, and preferably in the range of from 9 to 13 to form an alkaline crystallization mother liquor. The pH can be increased by the addition of a suitable base, for example KOH, NaOH, pyridine, triethylamine (TEA), $Mg(OH)_2$, $NH_4OH$ etc. The addition of the base results in a salt of mesotrione being formed which has a high solubility, ensuring that mesotrione is fully solubilized and that no mesotrione remains out of solution. In one embodiment, the base comprises KOH. In another embodiment, the base comprises KOH and no solvent is required and, thus, preferably not used.

The crystallizer is initially charged with an aqueous slurry containing at least 5% by weight, more preferably greater than 7% by weight, mesotrione crystals. The mesotrione crystals present in the slurry are predominantly mesotrione crystals of Form 1, that is, at least 80%, preferably at least 90%, more preferably at least 95%, by weight of the mesotrione crystals in the aqueous slurry are of Form 1. The alkaline crystallization mother liquor is then metered into the crystallizer, the pH is maintained at $\leq 4.0$. Suitably, the pH is adjusted to pH $\leq 3.5$ and preferably to pH $3\pm 0.5$.

The adjustment in pH is suitably carried out by the addition of acid to the mesotrione solution. Suitably, the acid comprises at least one member selected from the group consisting of HCl, $H_2SO_4$, $HNO_3$ etc; preferably HCl.

In certain cases, for example at a pH of 4.0 or slightly below, an increase in temperature can aid crytallization of Form 1.

Suitably, the process is carried out at a temperature of $\geq 25°$ C., preferably $\geq 40°$ C.

A second aspect of the invention provides a process for converting Form 2 mesotrione to Form 1 mesotrione. Occasionally it becomes desirable or necessary to re-crystallize a mesotrione product because it contains unacceptable levels of Form 2 mesotrione. In these situations, mesotrione is mixed with water to make a slurry. The pH of the slurry containing unacceptable levels of Form 2 mesotrione is first increased to a pH of >7, suitably $\geq 9$, and preferably in the range of from 9 to 13. The pH can be increased by the addition of a suitable base, for example KOH, NaOH, pyridine, triethylamine (TEA), $Mg(OH)_2$, $NH_4OH$ etc. The addition of the base results in a salt of mesotrione being formed, which has a high solubility, resulting in the Form 2 mesotrione going into solution. The solution is then charged to a crystallizer containing at least 5% by weight, preferably greater than 7% by weight mesotrione crystals predominantly of Form 1 while maintaining the pH in the crystallizer at 4.0 or below.

If this solution is crystallized in a batch mode, it produces the undesirable Form 2 crystals, unless acetonitrile or other solvents are added. However, if the crystallization of this material is conducted in a semi-continuous or continuous mode, even in the absence of solvents, the resulting product will consist predominantly of Form 1 crystals.

In one embodiment of this aspect of the invention, the Form 2 mesotrione has previously been isolated and is resuspended in, for example, water.

In one embodiment of this aspect of the invention, the Form 2 mesotrione has been formed as a result of the manufacturing process, and has not been isolated; and is therefore already suspended in the mother liquor.

As discussed hereinbefore, the invention arises from the realization that a semi-continuous or continuous crystallization process containing a high concentration of crystals having the desired morphological characteristics can be used to control the formation of one particular polymorph over the other or to convert one polymorph to the other.

In the semi-continuous crystallization process of the present invention the crystallizer is initially charged with an aqueous slurry containing at least 5% by weight, more preferably greater than 7% by weight, mesotrione crystals. The mesotrione crystals present in the slurry are predominantly mesotrione crystals of Form 1, that is, at least 80%, preferably at least 90%, more preferably at least 95%, by weight of the mesotrione crystals in the aqueous slurry are of Form 1. Typically, the crystallizer is charged with the aqueous slurry in an amount of at least 10% by volume of the crystallizer's capacity up to about 50% by volume of the crystallizer's capacity. The pH of the slurry is between 2.5 and 4.0, preferably between 2.5 and 3.5. The mesotrione solution at a pH greater than 7 preferably between 9 and 13 is pumped to the crystallizer at a controlled rate. The pH in the crystallizer is preferably maintained between 2.5 and 4.0, preferably between 2.5 and 3.5, by addition of an acid, such as 10% HCl. When the level in the crystallizer reaches an upper limit, for example 80% of the crystallizer capacity, the mesotrione feed is stopped. Mesotrione slurry is removed from the crystallizer until the volume reaches the lower limit, typically 10 to 20%, of the crystallizer capacity. The mesotrione feed is then restarted. In this mode of operation, the mesotrione crystals are of the desired Form 1 crystal morphology, even when re-dissolved mesotrione is crystallized.

In one embodiment, the present invention is directed to a semi-continuous crystallization process for preparing the Form 1 polymorph of mesotrione, said process comprising
  a) initially charging a crystallizer with an aqueous slurry containing at least 5% by weight mesotrione crystals, wherein at least 80% by weight of the mesotrione crystals present in the slurry are of Form 1;
  b) feeding a mesotrione solution at a pH greater than 7 to the crystallizer at a controlled rate while maintaining the pH in the crystallizer between 2.5 and 4.0 by addition of an acid;
  c) stopping the feed of the mesotrione solution when the level in the crystallizer reaches an upper limit;
  d) removing the mesotrione slurry from the crystallizer until the volume reaches a lower limit of the crystallizer capacity; and optionally
  e) restarting the mesotrione solution feed of b).

In the continuous crystallization process of the present invention the crystallizer is initially charged with an aqueous slurry containing at least 5% by weight, more preferably greater than 7% by weight, mesotrione crystals. The mesotrione crystals present in the slurry are predominantly mesotrione crystals of Form 1, that is, at least 80%, preferably at least 90%, more preferably at least 95%, by weight of the mesotrione crystals in the aqueous slurry are of Form 1. Typically, the crystallizer is initially charged with the aqueous slurry in an amount of at least 10% by volume of the crystallizer's capacity up to about 50% by volume of the crystallizer's capacity. The pH of the slurry is preferably between 2.5 and 4.0, preferably between 2.5 and 3.5. The mesotrione solution at a pH of greater than 7, preferably between 9 and 13 is pumped to the crystallizer at a controlled rate. The pH of the crystallizer is maintained between 2.5 and 4.0, preferably between 2.5 and 3.5, by addition of an acid, such as 10% HCl. When the liquid level in the crystallizer reaches the desired operating level, the volume of the crystallizer is maintained at that (a constant) level by continuously removing an appropriate amount of slurry. In this mode of operation, the mesotrione crystals are of the desired Form 1 crystal morphology, even when re-dissolved mesotrione is crystallized.

In one embodiment, the present invention is directed to a continuous crystallization process for preparing the Form 1 polymorph of mesotrione, said process comprising
a) initially charging a crystallizer with an aqueous slurry containing at least 5% by weight mesotrione crystals, wherein at least 80% by weight of the mesotrione crystals present in the slurry are of Form 1;
b) feeding a mesotrione solution at a pH greater than 7 to the crystallizer at a controlled rate while maintaining the pH in the crystallizer between 2.5 and 4.0 by addition of an acid; and
c) maintaining the volume of the crystallizer at a constant level by continuously removing an appropriate amount of slung.

FIG. 1 is the PXRD pattern for Form 1 mesotrione. The PXRD data for Form 1 mesotrione is set forth in Table 1.

TABLE 1

PXRD Data for Form 1 mesotrione.

| Peak Position (2-Theta) | Peak Position (d spacing) | Counts |
| --- | --- | --- |
| 8.52 | 10.34 | 13753 |
| 17.08 | 5.18 | 53322 |
| 17.43 | 5.08 | 39907 |
| 18.74 | 4.73 | 10146 |
| 19.04 | 4.66 | 8680 |
| 19.31 | 4.59 | 9582 |
| 19.52 | 4.54 | 7440 |
| 21.15 | 4.20 | 23786 |
| 25.73 | 3.46 | 42162 |
| 28.66 | 3.11 | 21081 |

Figure 2:
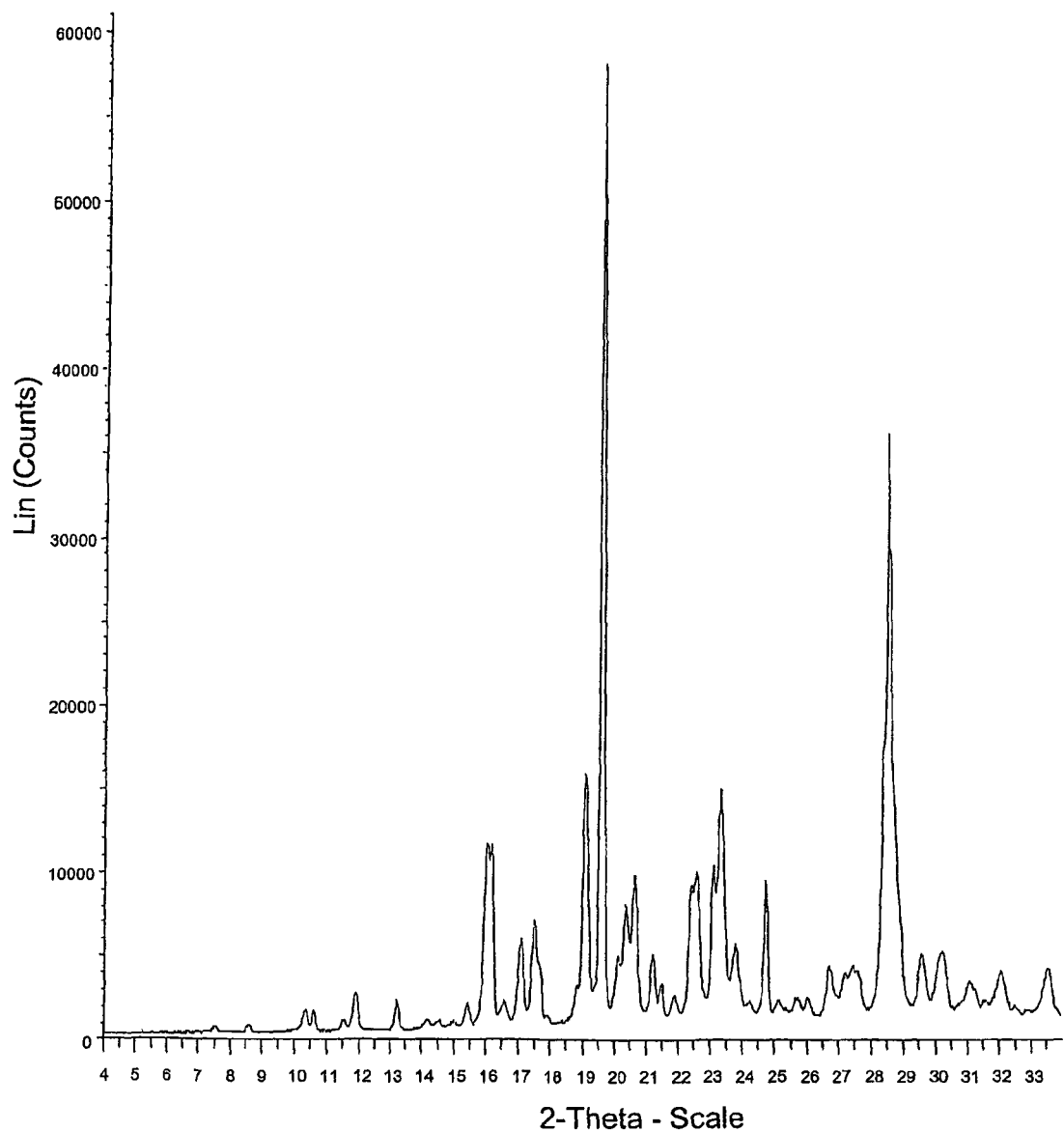
FIG. 2 is a powder X Ray diffraction (PXRD) pattern of Form 2 mesotrione.

FIG. 2 is the PXRD pattern for Form 2 mesotrione. The PXRD data for Form 2 mesotrione is set forth in Table 2.

TABLE 2

PXRD Data for Form 2 mesotrione.

| Peak Position (2-Theta) | Peak Position (d) | Counts |
| --- | --- | --- |
| 16.03 | 5.53 | 11611 |
| 16.19 | 5.47 | 11724 |
| 17.08 | 5.19 | 6426 |
| 17.49 | 5.07 | 7102 |
| 19.06 | 4.65 | 15782 |
| 19.61 | 4.52 | 58170 |
| 20.36 | 4.36 | 8117 |
| 20.64 | 4.30 | 9695 |
| 23.35 | 3.81 | 14881 |
| 28.53 | 3.13 | 36187 |

The following examples illustrate further some of the aspects of the invention but are not intended to limit its scope. Where not otherwise specified throughout this specification and claims, percentages are by weight.

EXAMPLES

Example 1

Batch Crystallization without Solvent

This comparative example outside of the scope of the present invention demonstrates that batch crystallization of a solution of re-dissolved Mesotrione crystals results in the formation of Form 2 crystals.

17 g of Mesotrione crystals were added to a crystallization reactor that contained 200 g of water. Next, 9.9 g of a 25% NaOH solution were added to raise the pH to 12.9 and to dissolve the Mesotrione crystals. The temperature was controlled at 25° C. by pumping water from a circulating water bath to the jacket of the reactor. The pH was then slowly lowered by pumping 10% HCl at a controlled rate to the crystallizer. When the pH reached approximately 9.5, the temperature was raised to 40° C. The acid addition was then resumed at a slow controlled rate until the pH reached 2.5. Analysis of the crystals indicated that they were Form 2 crystals.

Example 2

Batch Crystallization with Solvent

This comparative example outside of the scope of the present invention demonstrates that addition of 5% acetonitrile to re-dissolved Mesotrione will make Form 1 crystals in the batch crystallization process.

17 g of Mesotrione crystals (0.05 moles) were added to a crystallization reactor that contained 200 g of water. Next, 21 ml of TEA (0.15 moles) and 11 ml acetonitrile were added. TEA was added to more closely simulate the main components of the real process solution. In previous tests it was established that addition of TEA alone without acetonitrile resulted in Form 2 crystals. The pH was lowered with HCl to about 4.5, and raised again with a 25% NaOH solution to 12. The purpose of this step was to more closely reflect the conditions that occur in the manufacturing process. The temperature was controlled at 25° C. The pH was then slowly lowered by pumping 10% HCl at a controlled rate to the crystallizer. When the pH reached approximately 9.5, the temperature was raised to 40° C. The acid addition was then resumed at a controlled rate until the pH reached 2.8. Analysis of the crystals indicated that they were Form 1 crystals.

Example 3

Semi-Continuous Crystallization without Solvent; Mesotrione Dissolved with NaOH

This example demonstrates that re-dissolved Mesotrione can be crystallized in a semi-continuous mode to make Form 1 crystals without using solvents. NaOH was used to dissolve mesotrione crystals that were used as feed solution to the crystallizer.

An 8% slurry of Mesotrione was prepared by adding 32 g of Mesotrione to 400 g of water. The pH of the slurry was slowly raised to 9 with 20% NaOH to dissolve the Mesotrione crystals. The resulting solution was used as feed for the semi-continuous crystallization. Separately, a Mesotrione seed slurry was prepared by adding 8 g of wet crystals predominantly of Form 1 to the crystallization reactor together with 80 g water. The temperature of the crystallizer was controlled at 40° C. The pH in the crystallizer was controlled automatically at a setpoint of 2.9 by addition of 10% HCl. The feed solution containing the dissolved Mesotrione was pumped to the reactor at a rate of approximately 1 ml/min. When the liquid volume in the reactor reached a level of approximately 250 ml, between 50 and 150 ml of the slurry was removed. This operation was repeated until a total volume of 1500 ml feed solution had been crystallized. Solids samples of the various slurry samples that had been collected from the crystallizer were analyzed for crystal morphology. The analysis of the solids indicated that they were Form 1 crystals.

Example 4

Semi-Continuous Crystallization without Solvent; Mesotrione Dissolved with TEA

This example demonstrates that re-dissolved Mesotrione can be crystallized in a semi-continuous mode to make Form 1 crystals without using solvents. TEA was used to dissolve mesotrione crystals that were used as feed solution to the crystallizer.

An 8% slurry of Mesotrione was prepared by adding 24 g of mesotrione to 300 g of water. The pH of the slurry was slowly raised with TEA until all the mesotrione crystals were dissolved. The resulting solution was used as feed for the semi-continuous crystallization. Separately, a mesotrione seed slurry was prepared by adding 10 g of wet mesotrione crystals to the crystallization reactor together with 100 g water. The temperature of the crystallizer was controlled at 40° C. The pH in the crystallizer was controlled automatically at a setpoint of 2.9 by addition of 10% HCl. The feed solution containing the dissolved mesotrione was pumped to the reactor at a rate of approximately 1 ml/min. When the liquid volume in the reactor reached a level between 250 ml and 400 ml, an appropriate amount of slurry was removed to bring the liquid level in the crystallizer down to 100 ml. This operation was repeated until a total volume of 1400 ml feed solution had been crystallized. Solids samples of the various slurry samples that had been collected from the crystallizer were analyzed for crystal morphology. The analysis of the solids indicated that they were Form 1 crystals.

Example 5

Semi-Continuous Crystallization without Solvent; Mesotrione Solution from Manufacturing Plant In this example the semi-continuous crystallization process was applied to a Mesotrione solution obtained from the manufacturing plant. The crystallized product consisted of Form 1 crystals.

A mesotrione solution was obtained from the manufacturing plant. The sample was collected upstream of the plant crystallizer. The pH of the sample was adjusted to 9 by adding an appropriate amount of a 25% NaOH solution. This solution was the feed for the semi-continuous crystallizer. Separately, a mesotrione seed slurry was prepared by adding 8 g mesotrione crystals to the crystallization reactor together with 100 g water. The temperature of the crystallizer was controlled at 40° C. The pH in the crystallizer was controlled automatically at a setpoint of 2.9 by addition of 10% HCl. The feed solution containing the dissolved mesotrione was pumped to the reactor at a rate of approximately 1.7 ml/min. When the liquid volume in the reactor reached a level of approximately 325 ml, an appropriate amount of slurry was removed to bring the liquid level in the crystallizer down to 100 ml. This operation was repeated until a total volume of 2400 ml feed solution had been crystallized. Solids samples of the various slurry samples that had been collected from the crystallizer were analyzed for crystal morphology. The analysis of the solids indicated that they were Form 1 crystals.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

I claim:

1. A semi-continuous crystallization process for preparing the Form 1 polymorph of mesotrione, said process comprising
   a) initially charging a crystallizer with an aqueous slurry containing at least 5% by weight mesotrione crystals, wherein at least 80% by weight of the mesotrione crystals present in the slurry are of Form 1;
   b) feeding a mesotrione solution at a pH greater than 7 to the crystallizer at a controlled rate while maintaining the pH in the crystallizer between 2.5 and 4.0 by addition of an acid;
   c) stopping the feed of the mesotrione solution when the level in the crystallizer reaches an upper limit;
   d) removing the mesotrione slurry from the crystallizer until the volume reaches a lower limit of the crystallizer capacity; and optionally
   e) restarting the mesotrione solution feed of b).

2. The semi-continuous process of claim 1, wherein the crystallizer is charged with an aqueous slurry in an amount of at least 10% by volume of the crystallizer's capacity.

3. A continuous crystallization process for preparing the Form 1 polymorph of mesotrione, said process comprising
   a) initially charging a crystallizer with an aqueous slurry containing at least 5% by weight mesotrione crystals, wherein at least 80% by weight of the mesotrione crystals present in the slurry are of Form 1;
   b) feeding a mesotrione solution at a pH greater than 7 to the crystallizer at a controlled rate while maintaining the pH in the crystallizer between 2.5 and 4.0 by addition of an acid; and
   c) maintaining the volume of the crystallizer at a constant level by continuously removing an appropriate amount of slurry.

* * * * *